United States Patent [19]
Langer et al.

[11] Patent Number: 5,966,692
[45] Date of Patent: Oct. 12, 1999

[54] METHOD AND SYSTEM FOR MONITORING THE HEART OF A PATIENT

[75] Inventors: Alois A. Langer, Pittsburgh; Khalil J. Maalouf, Turtle Creek, both of Pa.

[73] Assignee: Telemed Technologies International Corporation, Turtle Creek, Pa.

[21] Appl. No.: 08/950,464

[22] Filed: Oct. 15, 1997

Related U.S. Application Data

[63] Continuation of application No. 08/733,262, Oct. 18, 1996, abandoned, which is a continuation of application No. 07/881,604, May 12, 1992, abandoned.

[51] Int. Cl.⁶ .............................................. A61B 5/0402
[52] U.S. Cl. .............................. 705/3; 600/509; 600/522
[58] Field of Search .......................... 705/2, 3; 600/500, 600/508, 509, 513, 515, 522, 523; 340/531, 539, 573; 607/5, 9

[56] References Cited

U.S. PATENT DOCUMENTS

| | | | |
|---|---|---|---|
| 3,724,455 | 4/1973 | Unger | 128/702 |
| 3,882,277 | 5/1975 | DePedro et al. | 379/106 |
| 4,102,332 | 7/1978 | Gessman | 128/700 |
| 4,173,971 | 11/1979 | Karz | 128/702 |
| 4,184,493 | 1/1980 | Langer et al. | 607/5 |
| 4,202,340 | 5/1980 | Langer et al. | 607/5 |
| 4,221,223 | 9/1980 | Linden | 128/706 |
| 4,340,065 | 7/1982 | Gessman | 128/712 |
| 4,494,552 | 1/1985 | Heath | 128/696 |
| 4,622,979 | 11/1986 | Katchis et al. | 128/702 |
| 4,625,276 | 11/1986 | Benton et al. | 364/408 |
| 4,630,204 | 12/1986 | Mortara | 364/413.06 |
| 4,792,796 | 12/1988 | Bradshaw et al. | 340/539 |
| 4,803,625 | 2/1989 | Fu et al. | 364/413.03 |
| 4,851,820 | 7/1989 | Fernandez | 340/825.44 |
| 4,945,477 | 7/1990 | Edwards | 364/413.06 |
| 4,974,251 | 11/1990 | Ohta et al. | 379/61 |
| 4,981,139 | 1/1991 | Pfohl | 128/671 |
| 5,012,411 | 4/1991 | Policastro et al. | 364/413.06 |
| 5,111,396 | 5/1992 | Mills et al. | 364/413.06 |
| 5,113,869 | 5/1992 | Nappholz et al. | 128/696 |
| 5,157,604 | 10/1992 | Axford et al. | 364/413.03 |
| 5,291,399 | 3/1994 | Chaco | 364/413.02 |
| 5,321,618 | 6/1994 | Gessman | 364/413.06 |
| 5,331,549 | 7/1994 | Crawford, Jr. | 364/413.01 |
| 5,335,664 | 8/1994 | Nagashima | 128/696 |

OTHER PUBLICATIONS

IBM Technical Disclosure Bulletin, vol. 25, No. 7A, Dec. 1982, *Portable ECG Event Detector*, by R.E. Bonner pp. 3412–3413.

*Primary Examiner*—Stephen R Tkacs
*Attorney, Agent, or Firm*—Ansel M. Schwartz

[57] ABSTRACT

A system for monitoring the heart of a patient. The system is comprised of a remote station having a device for generating an electrocardiogram of the patient, a device for detecting predetermined cardiological events in the patient in communication with the generating device and a transmitter for transmitting the electrocardiogram. The system also is comprised of a central station in continuous communication with the transmitter for receiving the transmitted electrocardiogram when a predetermined cardiological event occurs. There is also a database in communication with the central station for storing patient data and providing patient data to the central station. Additionally, there is a display device in communication with the central station and the database for displaying the patient data and the transmitted electrocardiogram. A method of monitoring the heart of a patient. The method includes the first step of taking an electrocardiogram of a patient at a remote station. Then, there is the step of automatically detecting predetermined cardiological events in the electrocardiogram. Next, there is the step of transmitting the electrocardiogram to a central station along with identification of the patient if a predetermined cardiological event occurs and immediately after it occurs. Then, there is the step of retrieving data about the patient from a database in communication with the central station. Next, there is the step of transmitting the patient's data to the central station.

20 Claims, 4 Drawing Sheets

METHOD AND SYSTEM FOR MONITORING THE HEART OF A PATIENT

This application is a continuation of application Ser. No. 08/733,262, filed on Oct. 18, 1996, now abandoned which is a continuation of Ser. No. 07/881,604 filed on May 12, 1992, now abandoned.

FIELD OF THE INVENTION

The present invention is related in general to heart monitors. More specifically, the present invention is related to a method and system which monitors a patient's heart and provides an electrocardiogram and data of the patient to a central station when a predetermined cardiological event occurs.

BACKGROUND OF THE INVENTION

Heart malfunction is one of the primary causes of death in humans. In order to detect and predict heart malfunctions, it is known to connect patients to a heart monitor. Typical heart monitors generate and display an electrocardiogram of the heartbeat and are directly connected to the patient with electrodes. Unfortunately, these heart monitors require the patient to reside in the hospital in dedicated telemetric beds. Further, the multitude of state of the art heart monitors necessary to monitor the often numerous heart patients represent undue complexity and expense. U.S. Pat. No. 4,173,971 by Karz, incorporated by reference, discloses a system for sending an electrocardiogram to a remote location, but does not provide for further support to assist in the response to a patient in need.

SUMMARY OF THE INVENTION

The present invention pertains to a system for monitoring the heart of a patient. The system is comprised of a remote station having means for generating an electrocardiogram of the patient, means for detecting predetermined cardiological events in the patient in communication with the generating means and a transmitter for transmitting the electrocardiogram. The system also is comprised of a central station in communication with the transmitter for receiving the transmitted electrocardiogram when a predetermined cardiological event occurs. There is also a database in communication with the central station for storing patient data and providing patient data to the central station. Additionally, there is display means in communication with the central station and the database for displaying the patient data and the transmitted electrocardiogram.

The invention is also a method of monitoring the heart of a patient. The method includes the first step of taking an electrocardiogram of a patient at a remote station. Then, there is the step of automatically detecting predetermined cardiological events in the electrocardiogram. Next, there is the step of transmitting the electrocardiogram to a central station along with identification of the patient if a predetermined cardiological event occurs. Then, there is the step of retrieving data about the patient from a database in communication with the central station. Next, there is the step of transmitting the patient's data to the central station.

BRIEF DESCRIPTION OF THE DRAWINGS

In the accompanying drawings, the preferred embodiment of the invention and preferred methods of practicing the invention are illustrated in which.

DESCRIPTION OF THE PREFERRED EMBODIMENT

Figure 1:
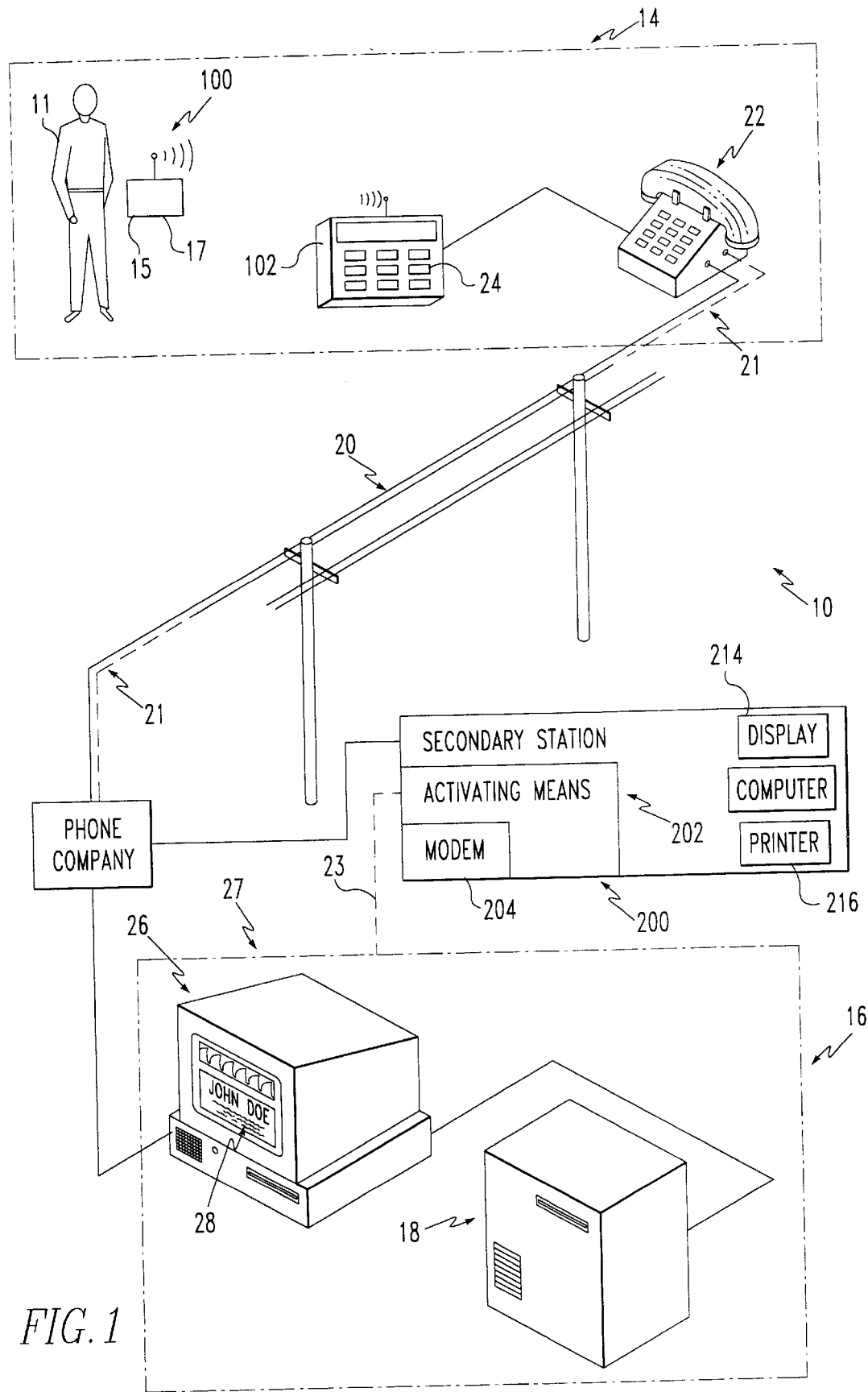
FIG. 1 is a schematic representation showing the system for monitoring the heart of a patient.

Referring now to the drawings wherein like reference numerals refer to similar or identical parts throughout the several views, and more specifically to FIG. 1 thereof, there is shown a system 10 for monitoring the heart 12 of a patient. The system 10 is comprised of a remote station 14 having means for generating an electrocardiogram of the patient, means for detecting predetermined cardiological events in the patient in communication with the generating means and a transmitter for transmitting the electrocardiogram. The system 10 additionally is comprised of a central station 16 in communication with the transmitter 14 for receiving the transmitted electrocardiogram. There is also a database 18 in communication with the central station for storing patient data and providing patient data to the central station 16. Additionally, there is display means in communication with the central station and the database for displaying the patient data and the transmitted electrocardiogram.

Figure 2:
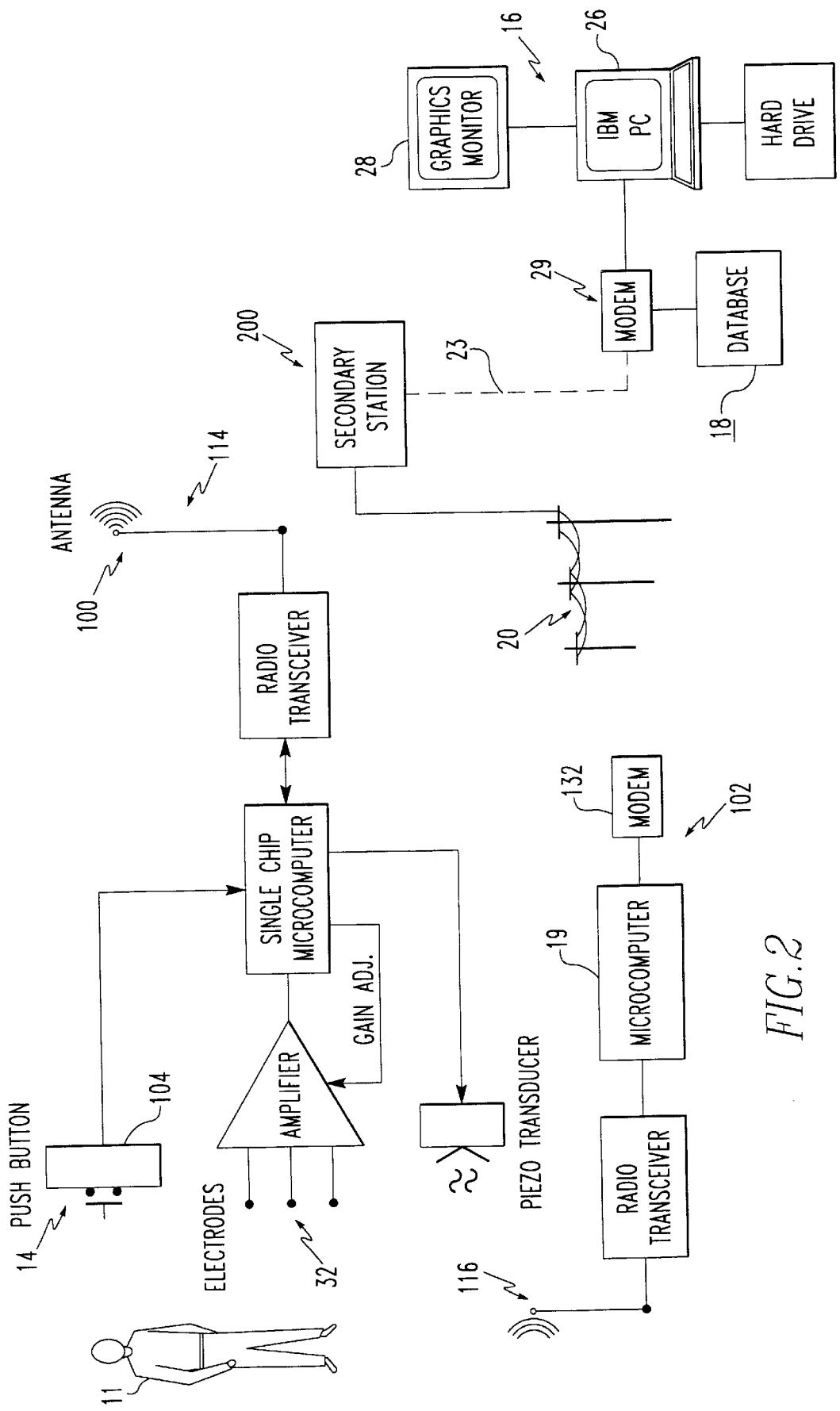
FIG. 2 is a schematic representation of a system for monitoring the heart of a patient.

In a preferred embodiment, and as shown in FIG. 2, the remote station 14 includes a small electronic unit called a patient transmitter 100 that is carried by the patient. The remote station 14 communicates with the central station 16 over a telecommunications line 20, preferably through the patient's own telephone 22 via a tele-link 102 of the remote station 14. The central station 16 has a central receiver or modem 19 for receiving the electrocardiogram from the telecommunications line 20. The remote station 14 has a keypad 24 for inputting information such as the hospital phone number and patient identification numbers.

It is also desirable for the central station 16 to communicate with the patient through the system 10. Accordingly, the central station 16 can include a central transmitter 21 for transmitting information from the central station 16 to the remote station 14 over the telecommunications line 20. The remote station 14 includes a remote receiver, such as a modem 132, for receiving information from the central station 16 over the telecommunications lines 20. Preferably, the central station 16 is located within the patient's hospital and includes a computer 26 and display screen 28. The central transmitter and receiver can also be a modem as mentioned above.

The invention is also a method of monitoring the heart of a patient. The method includes the first step of taking an electrocardiogram of a patient. Then, there is the step of automatically detecting predetermined cardiological events in the electrocardiogram. Next, there is the step of transmitting the electrocardiogram to a central station along with identification of the patient if a predetermined cardiological event occurred. Then, there is the step of retrieving data about the patient from a database. Next, there is the step of transmitting the patient's data from the database to the central station 16.

Preferably, the detecting step includes the step of automatically diagnosing the electrocardiogram. Preferably, after the retrieving step, there is the step of contacting the patient and after the diagnosing step, there is the step of sounding an alarm. Preferably, after the transmitting step, there is the step of displaying the electrocardiogram and the corresponding patient data on a display screen. Preferably, the transmitting step includes the step of transmitting the electrocardiogram over a telecommunication line and before the taking step, there is the step of programming the remote station with patient identification and the phone number of the central station.

In the operation of the preferred embodiment, a patient 11 who is in medical need of heart monitoring is assigned a remote station 14 from his doctor at the hospital. The remote station 14 is comprised of a patient transmitter 100 which is worn by the patient, and a tele-link 102 which is operationally connected to a telephone where the patient is located. The doctor then programs the remote station 14 with the patient's identification number and the phone number of the hospital's central station 16. A keypad 24 is provided on the remote station 14 for inputting the information. A display window 34 is provided for displaying the information. Once the remote station 14 is operational, it is set in a dormant state and the patient is allowed to go home. Alternatively, the patient can go to a hotel, a friend's home, other type of health care facility or even another room or bed in the hospital which does not have dedicated instrumentation to provide heart monitoring of the patient 11, to name but a few of the many remote stations to which the patient can go, as long as there is at least a phone nearby.

During its dormancy, the remote station 14 periodically activates to check if it is connected to the telecommunication line 20. Once home, the patient links the remote station 14 to the telephone line 20 and dials the phone number of the hospital's central station 16 to establish the connection with the central station 16. Electrodes 32 from the patient transmitter 100 of the remote station 14 are connected to the patient for monitoring his heart 12. The electrocardiogram signal generated by the patient transmitter 100 of the remote station 14 is analyzed by the first computer 17 having a computer program within the tele-link 102 to detect predetermined threshold events, such as arrythmia or tachycardia. The patient transmitter 102 can be a fully analog system as disclosed in U.S. Pat. No. 3,195,535 (incorporated by reference), which shows a complete miniature radiating electrocardiograph, or preferably, it can be digital transmitter which codes the electrocardiogram data into digital representation. In this preferred embodiment, the electrocardiogram amplifier 120 is similar to that in U.S. Pat. No. 3,724,455 by Ungar, incorporated by reference, at block 70, while the A–D and digital data compressor 122 is disclosed in U.S. Pat. No. 5,014,284 by Langer et al., incorporated by reference. A digital radio transmitter is known to one skilled in the art and an example is described in Motorola Application Note AN980 using FSK techniques. If a threshold event is detected, the remote station 14 calls the central station 16 and transmits the electrocardiogram to the central station 16.

The tele-link 102 comprises a radio receiver 126 similar to the aforementioned Ungar patent or if a digital radio receiver 128 is used, similar to the LAWN wireless modem product manufactured by O'Neill Communications, Princeton, N. J. Arrythmia analysis systems are well known and are mentioned in the Ungar U.S. Pat. No. 3,724,455 patent, or U.S. Pat. Nos. 3,536,062 and 4,221,223, both incorporated by reference, which measure heart rate and can provide an alarm if there is high heart rate, and U.S. Pat. Nos. 4,202,340 and 4,184,493 by Langer, incorporated by reference, which can detect Ventricular Fibrillation. U.S. Pat. No. 4,630,204, incorporated by reference, describes an electrocardiogram detection system. Modems 132, 19 are commonly found in today's computers and are manufactured by Hayes and others as well as being described in application notes by VLSI and Silicon Systems, semiconductor chip manufactures. The use of an autodialer to send electrocardiogram data is disclosed in U.S. Pat. No. 4,102,332 by Gessman, incorporated by reference. A DAA 134 (direct access arrangement) is necessary to connect to the phone line.

Figure 3:
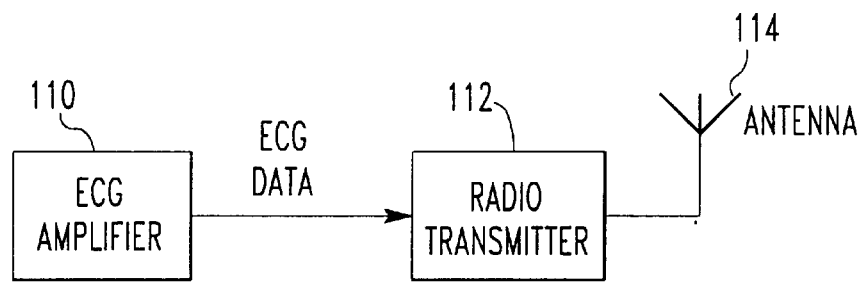
FIG. 3 is a schematic representation of an analog embodiment of a patient transmitter.

More specifically, when the patient transmitter 102 is a fully analog system as shown in FIG. 3, the electrocardiogram amplifier 110 takes the electrocardiogram from the electrodes 32 and amplifies the signal, which it then provides to the radio transmitter 112. The radio transmitter 112 then transmits it by way of antenna 114, to the tele-link 102.

Figure 4:
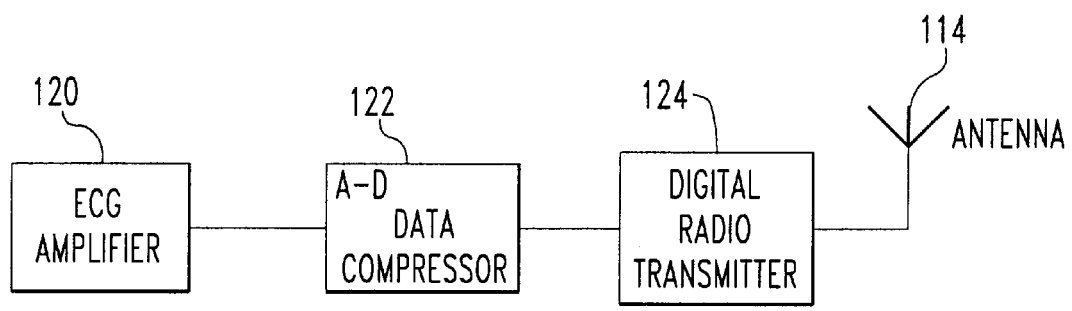
FIG. 4 is a schematic representation of a digital embodiment of a patient transmitter.

If the electrocardiograph signal is transmitted digitally, then the electrocardiogram amplifier 120, as shown in FIG. 4, receives the electrocardiograph signal from electrodes 32, amplifies it and provides it to an analog to digital and data compressor 122 which is essentially a single chip microcomputer. The digitized compressed signal is then provided to a digital radio transmitter 124 which transmits the signal via antenna 114 to antenna 116 of the tele-link 102.

Figure 5:
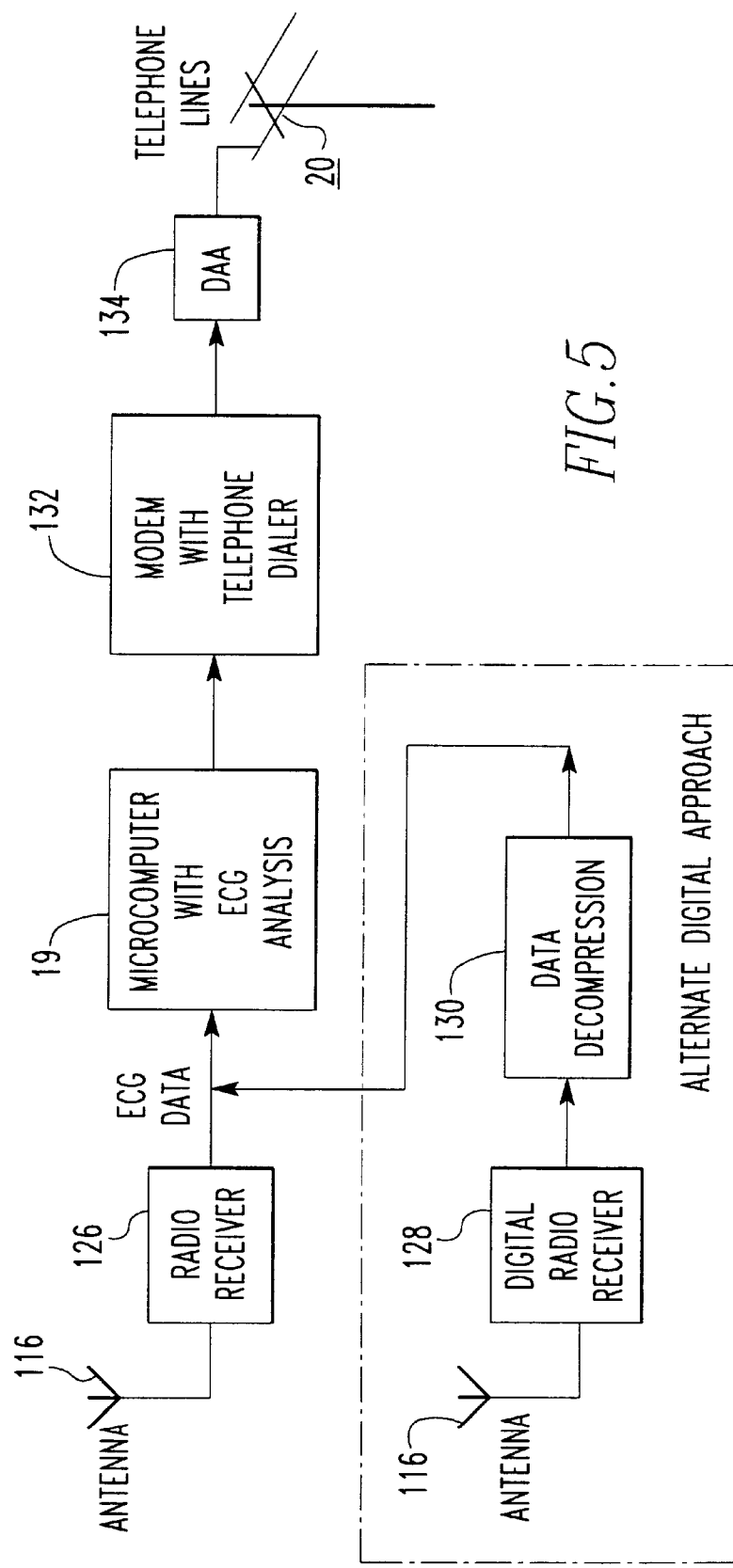
FIG. 5 is a schematic representation of an analog and alternate digital embodiment to a tele-link.

With respect to the tele-link 102 as shown in FIG. 5, the radio receiver 126 receives the transmitted signal from antenna 116 and provides a signal to the first computer 17 which has electrocardiogram analysis. If the signal has been digitized, then the alternate digital approach as shown in FIG. 5 is utilized where a digital radio receiver 128 receives the signal from antenna 116 and provides it to a data decompressor 130 which decompresses the signal so the first computer 17 can analyze the signal. If a predetermined cardiological event is determined to have occurred by the first computer 17, then the electrocardiogram which has already been compressed is provided through a modem with an autodialer 132 through a DAA 134 to the telephone lines 20. The first computer 17 operates the telecommunications linkage.

Audio and visual alarms on the central station 16 are then activated to alert the proper medical personnel at the hospital. The second computer 26 retrieves data on the patient having a threshold event from the database 18 and displays it on the display screen 28 along with the electrocardiogram and its diagnosis by the first computer 17. The patient data contains a medical history, prescribed drugs and instructions on what to do for critical heartbeat irregularities. The second computer 26 also constructs an alarm table which includes past occurrences of diagnosed threshold events and prescribed responses thereto. A doctor then analyzes the data of the central station 16 and comes to a judgment as for what medical action should be taken. If for example, the doctor ascertains that the patient is in danger, he can call the patient directly through the system 10 and/or send for ambulatory transport.

If the patient 11 wishes to manually cause his electrocardiogram to be recorded, as opposed to it only being recorded when a threshold event is identified by the first computer 17, he pushes a button 104 and holds it until a beep is produced by the microprocessor 101. The recorded electrocardiogram can be stored in memory in the first computer 17 to be used when desired. Additionally, the microprocessor 101 is programmed to sound a beep whenever the patient 11 is out of range of the tele-link 102.

Although the invention has been described in detail in the foregoing embodiments for the purpose of illustration, it is to be understood that such detail is solely for that purpose and that variations can be made therein by those skilled in the art without departing from the spirit and scope of the invention except as it ay be described by the following claims.

What is claimed is:

1. A method of outpatient monitoring the heart of a patient comprising the steps of:

taking an electrocardiogram of a patient at a remote station;

automatically detecting predetermined cardiological events in the electrocardiogram;

automatically transmitting the electrocardiogram to a central station remote from the patient at the remote station along with identification of the patient if a predetermined cardiological event has occurred and promptly after it has occurred;

automatically retrieving data, including non-physiological data, about the patient having a predetermined cardiological event from a database in communication with the central station; and automatically transmitting the data to the central station from the database for presenting at least some of the electrocardiogram and data about the patient to the central station.

2. A method as described in claim 1 wherein the detecting step includes the step of automatically diagnosing the electrocardiogram.

3. A method as described in claim 1 wherein the detecting step occurs at the remote station remote from the central station.

4. A method as described in claim 3 wherein after the transmitting step, there is the step of displaying the electrocardiogram and the corresponding patient data at the central station.

5. A method as described in claim 1 wherein the electrocardiogram transmitting step includes the step of automatically transmitting the electrocardiogram over a telecommunication line and before the taking step, there is the step of programming the remote station with patient identification and a phone number of the central station.

6. A method as described in claim 1 wherein before the step of transmitting the electrocardiogram, there is the step of automatically dialing the telephone number of the central station to form a telephone connection between the central station and the patient.

7. A method as described in claim 1 wherein after the diagnosing step, there is the step of sounding an alarm.

8. A method as described in claim 1 wherein after the retrieving step, there is the step of contacting the patient.

9. A method as described in claim 1 wherein the step of taking an electrocardiogram comprises the step of continuously monitoring the electrocardiogram of the patient.

10. A method as described in claim 9 wherein the step of taking an electrocardiogram comprises the step of continuously monitoring the electrocardiogram of the patient with a patient transmitter continuously worn by the patient and transmitting the electrocardiogram with an antenna to a tele-link of the remote station.

11. A method as described in claim 10 wherein the step of automatically detecting predetermined cardiological events comprises the step of analyzing the electrocardiogram with a computer program for threshold events.

12. A system for outpatient monitoring the heart of a patient comprising:

a remote station having means for generating an electrocardiogram of a patient, means for detecting predetermined cardiological events in the electrocardiogram in continuous communication with the generating means, and a transmitter for promptly transmitting the electrocardiogram when a predetermined cardiological event occurs in the patient;

a central station in communication with the transmitter for receiving the transmitted electrocardiogram;

a database in communication with the central station for storing and providing patient data, including non-physiological data, to the central station when a predetermined cardiological event occurs; and display means in communication with the central station and the database for displaying at least some of the patient data and the transmitted electrocardiogram.

13. A system as described in claim 12 including a telecommunication line, and wherein the central station has a central receiver for receiving the electrocardiogram from the telecommunication line, said receiver in communication with said telephone line.

14. A system as described in claim 13 wherein the central station includes a central transmitter for transmitting information to the remote station over the telecommunications line, and the remote station includes a remote receiver for receiving information from the central station over the telecommunications line.

15. A system as described in claim 14 wherein the detecting means includes a first computer having a program which analyzes the electrocardiogram and causes the electrocardiogram to be transmitted when a predetermined cardiological event occurs.

16. A system as described in claim 15 wherein the central station includes a second computer, and the display means includes a display screen electrically connected to th e second computer.

17. A system as described in claim 16 wherein the remote station has a keypad for inputting information.

18. A system as described in claim 12 wherein the electrocardiogram generating means comprises means for continually monitoring the electrocardiogram of the patient.

19. A system as described in claim 18 wherein remote station includes a patient transmitter which is continuously worn by the patient and continuously generates the electrocardiogram and a tele-link which communicates with the patient transmitter with an antenna.

20. A system as described in claim 19 wherein the remote station comprises a computer program for analyzing the electrocardiogram for threshold events.

\* \* \* \* \*